United States Patent [19]

Matsushima et al.

[11] 4,145,530

[45] Mar. 20, 1979

[54] 2'-DEAMINO-3'-EPIAMINO-3'-DEOXY-XK-88-5 AND PROCESS FOR THE PRODUCTION THEREOF

[75] Inventors: Hideo Matsushima, Machida; Yasuki Mori, Kawasaki, both of Japan

[73] Assignee: Abbott Laboratories, North Chicago, Ill.

[21] Appl. No.: 863,628

[22] Filed: Dec. 23, 1977

[30] Foreign Application Priority Data

Dec. 24, 1976 [JP] Japan .................... 51-154900

[51] Int. Cl.$^2$ ...................... C07H 15/22; A61K 31/71
[52] U.S. Cl. ........................... 536/17; 424/180
[58] Field of Search ........................... 536/17

[56] References Cited

U.S. PATENT DOCUMENTS

| 3,997,524 | 12/1976 | Nagabhushan | 536/17 |
| 4,000,262 | 12/1976 | Daniels | 536/17 |
| 4,053,591 | 10/1977 | Daniels et al. | 536/17 |

Primary Examiner—Johnnie R. Brown
Attorney, Agent, or Firm—Fitzpatrick, Cella, Harper & Scinto

[57] ABSTRACT

A new antibiotic, 2'-deamino-3'-epiamino-3'-deoxy-XK-88-5 represented by the formula:

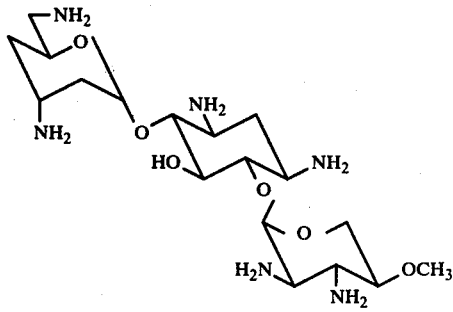

is produced by chemically modifying the antibiotic XK-88-5 represented by the formula:

2 Claims, 2 Drawing Figures

2'-DEAMINO-3'-EPIAMINO-3'-DEOXY-XK-88-5 AND PROCESS FOR THE PRODUCTION THEREOF

RELATED APPLICATIONS

The present invention is generally related to the inventions disclosed in U.S. Pat. No. 3,939,043 issued on Feb. 17, 1976 for a process for the production XK-88-5 series and U.S. Pat. No. 4,045,610 issued on Aug. 30, 1977 for Antibiotics designated XK-88 series and U.S. Patent Application Ser. No. 815,054, filed July 12, 1977 for 6-N-methyl-XK-88-5 and process for production thereof.

BACKGROUND OF THE INVENTION

The present invention relates to a derivative of the antibiotic XK-88-5 and more specifically relates to a new antibiotic, 2'-deamino-3'-epiamino-3'-deoxy-XK-88-5 and a process for the production thereof.

XK-88-5 is one factor of a series of related antibiotic compounds produced by culturing a microorganism such as Streptomyces hofuensis, ATCC 21970 under suitable conditions. The XK-88 series of antibiotics are also known as Seldomycins. Although XK-88-5 (Seldomycin Factor-5), exhibits good antibacterial activity, certain microorganisms have the ability to enzymatically inactivate the base compound.

Further, it is in demand to produce new derivatives of XK-88-5 useful as antibacterial agents.

It has now been found that a particular derivative of XK-88-5 is not susceptible to such enzymatic inactivation.

SUMMARY OF THE INVENTION

The present invention relates to a new derivative of the antibiotic XK-88-5, that is, 2'-deamino-3'-epiamino-3'-deoxy-XK-88-5 (Compound I) represented by the formula [I]:

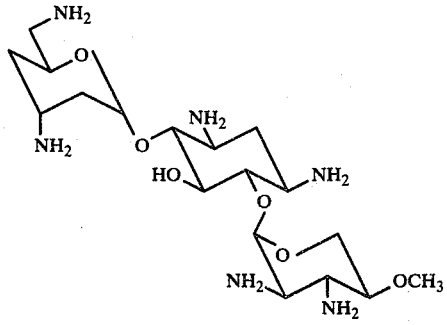

A new compound, 2'-deamino-3'-epiamino-3'-dexoy-XK-88-5, exhibits excellent broad spectrum of antibacterial activity and is also effective against microorganisms having the ability to enzymatically inactivate XK-88-5.

Included in the composition of matter aspect of the invention are the pharmaceutically acceptable, non-toxic acid addition salts of 2'-deamino-3'-epiamino-3'-deoxy-XK-88-5. Suitable acid addition salts are prepared in known manner by, for example, reacting one molecule of 2'-deamino-3'-epiamino-3'-deoxy-XK-88-5 with one to six equimole acid.

The process of the present invention is that of producing 2'-deamino-3'-epiamino-3'-deoxy-XK-88-5 which comprises eliminating the amino protecting groups $R_1$ and/or $R_2$ of a hexa-N-protected-2'-deamino-3'-epiamino-3'-deoxy-XK-88-5 (Compound II) represented by the general formula [II]:

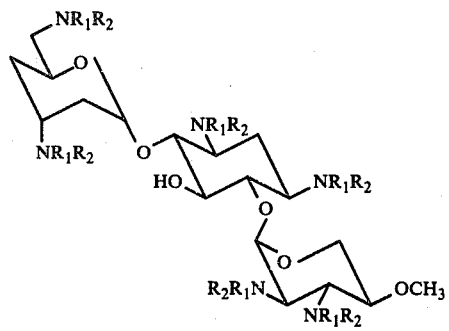

(wherein one of $R_1$ and $R_2$ is hydrogen and the other is an amino protecting group, or $R_1$ and $R_2$ is a protecting group as one body) in a known manner to prepare 2'-deamino-3'-epiamino-3'-deoxy-XK-88-5 (Compound I).

In this process, amino protecting groups such as acetyl, methoxycarbonyl, ethoxycarbonyl, benzyloxycarbonyl, benzyl, tertiary butyloxycarbonyl, amyloxycarbonyl, phthaloyl groups, etc. may be used.

The present inventors have found that 2'-deamino-3'-epiamino-3'-deoxy-XK-88-5 has excellent antibacterial activities against microorganisms having the ability to enzymatically inactive the base compound, XK-88-5.

The Compound II is obtained as a by-product in the process for preparing 3'-deoxy-XK-88-5 represented by the formula [III]:

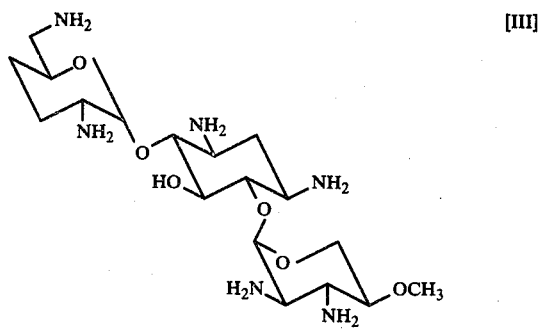

in which process XK-88-5 represented by the formula [IV]:

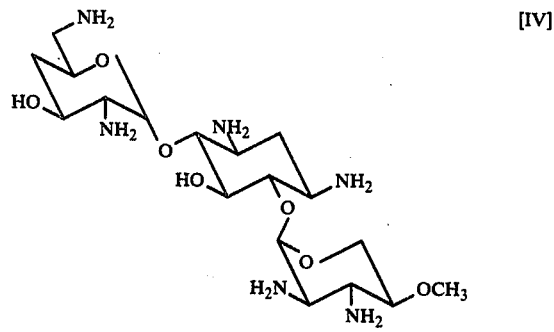

is used as a starting material. A process for preparing 3'-deoxy-XK-88-5 from XK-88-5 is also invented by the same inventors of this invention and is disclosed in Japanese Patent Application 97,914/76 filed on Aug. 17, 1976 by Kyowa Hakko Kogyo Co., Ltd.

The process is shown below.

The desired 2'-deamino-3'-epiamino-3'-deoxy-XK-88-5 is obtained by (A) protecting the amino groups of XK-88-5 (Compound IV) with an amino protecting agent to prepare a hexa-N-protected-XK-88-5 (Compound V) represented by the general formula [V]:

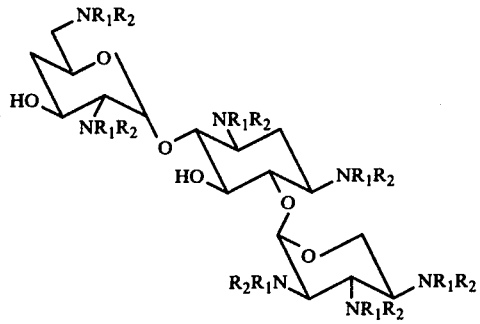

wherein $R_1$ and $R_2$ have the same significance as defined above, (B) reacting Compound (V) with a sulfonyl chloride represented by the general formula:

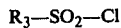

$R_3$—$SO_2$—Cl (wherein $R_3$ is methyl, phenyl, paramethylphenyl or parabromophenyl group) to prepare a hexa-N-protected-3'-0-sulfonyl-XK-88-5 (Compound VI) represented by the general formula [VI]:

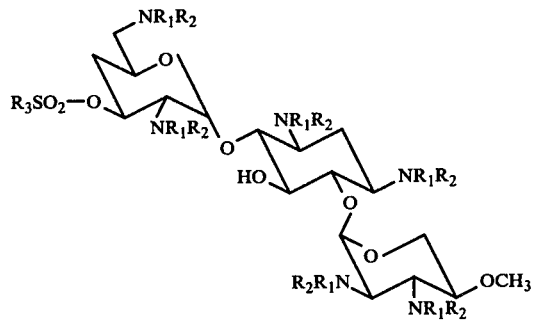

wherein $R_1$, $R_2$ and $R_3$ have the same significance as defined above, (C) reacting Compound VI with a metal hydride to prepare a hexa-N-protected-3'-deoxy-XK-88-5 (Compound VII) represented by the general formula [VII]:

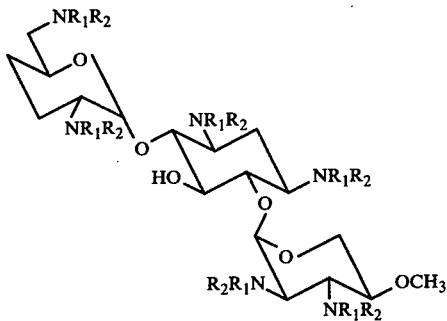

wherein $R_1$ and $R_2$ have the same significance as defined above, and thereafter (D) eliminating the amino protecting groups $R_1$ and/or $R_2$ of Compound VII in a known manner to prepare 3'-deoxy-XK-88-5 (Compound III).

According to further investigation of the reaction between Compound (VI) and a metal hydride, it has been found that Compound II is also formed in the reaction mixture and may be isolated therefrom.

Each signal of 2'-deamino-3'-epiamino-3'-deoxy-XK-88-5 is given below ($C_2'$ and $C_4'$ may be mutually exchangeable). The values are calculated from TMS standard, presuming the value of dioxane as 67.4 ppm.

| | | | | | | | |
|---|---|---|---|---|---|---|---|
| $C_1'$ | 100.4, | $C_2'$ | 36.6, | $C_3'$ | 42.9, | $C_4'$ | 35.4, |
| $C_5'$ | 69.1, | $C_6'$ | 44.9, | $C_1$ | 51.3, | $C_2$ | 36.9, |
| $C_3$ | 50.0, | $C_4$ | 88.0, | $C_5$ | 75.1, | $C_6$ | 86.9, |
| $C_1''$ | 100.4, | $C_2''$ | 56.2, | $C_3''$ | 54.9, | $C_4''$ | 80.3, |
| $C_5''$ | 60.7, | $OCH_3$ | 58.8 | (ppm) | | | |

DETAILED DESCRIPTION OF THE INVENTION

The physicochemical properties of the free base of 2'-deamino-3'-epiamino-3'-deoxy-XK-88-5 of the present invention are as follows:

1. A basic white powder
2. Melting point: 134°–137° C.
3. Specific rotation: $[\alpha]_D^{22} = +106°$ ($c=0.356$, water)
4. Elemental analysis as $C_{18}H_{38}N_6.H_2CO_3.H_2O$: Found (%): C = 44.75, H = 8.08, N = 16.55. Calculated (%): C = 44.34, H = 8.24, N = 16.33.
5. Rf value by silica gel thin layer chromatography is 0.83 presuming Rf value of XK-88-5 as 1.00. [developer; methanol:conc. aqueous ammonia: chloroform = 3:2:1 (by volume)]
6. Molecular weight determined by a high resolution— mass spectrometry: 434.2816
  mass spectrum m/e: 129, 145, 163, 272, 307

Figure 1:
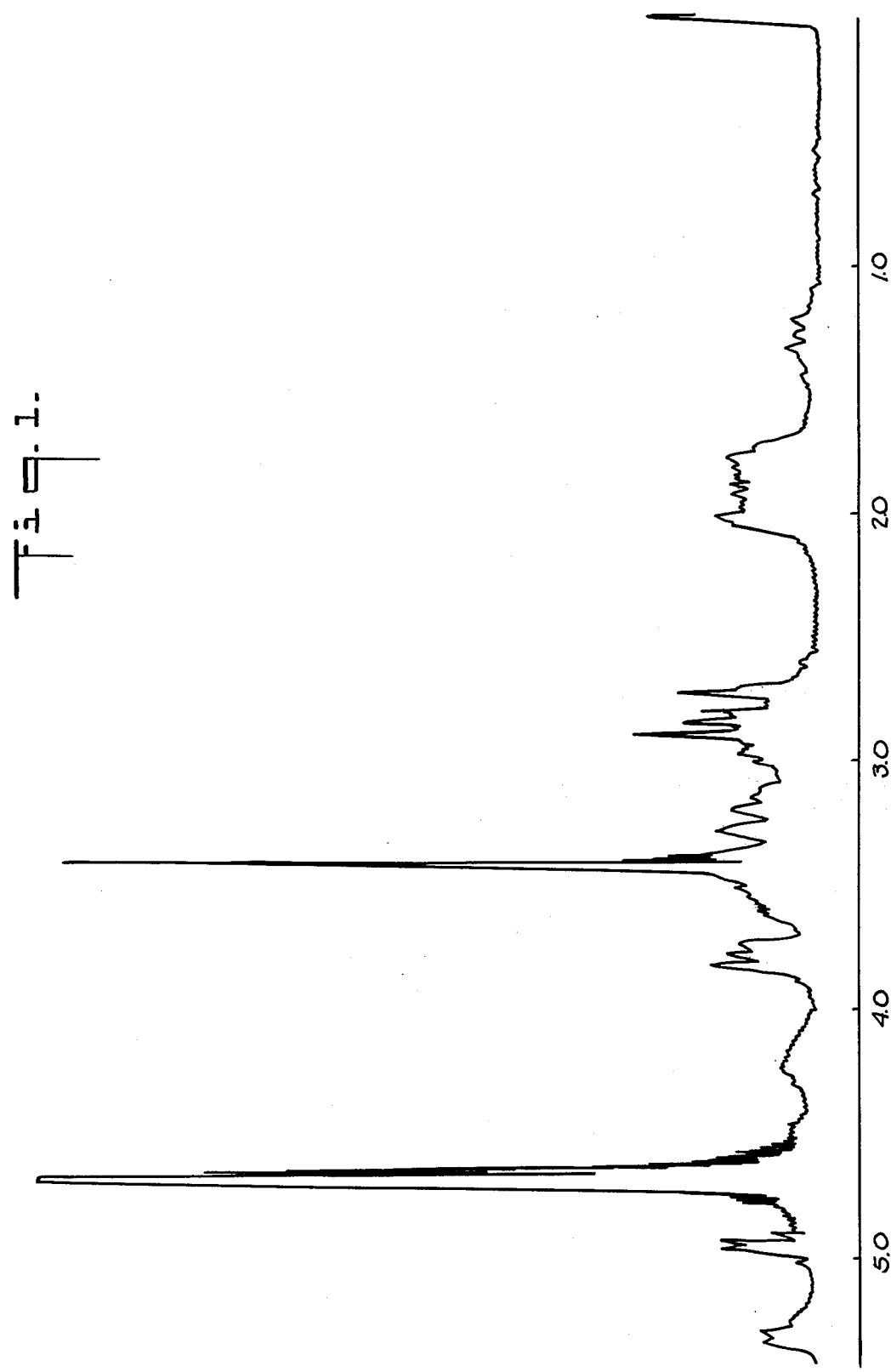
FIG. 1 shows PMR spectrum of 2'-deamino-3'-epiamino-3'-deoxy-XK-88-5 measured in deuterium oxide solution at PD 10.5 using sodium 4,4-dimethyl-4-silapentanesulfonate as an internal standard.
Figure 2:
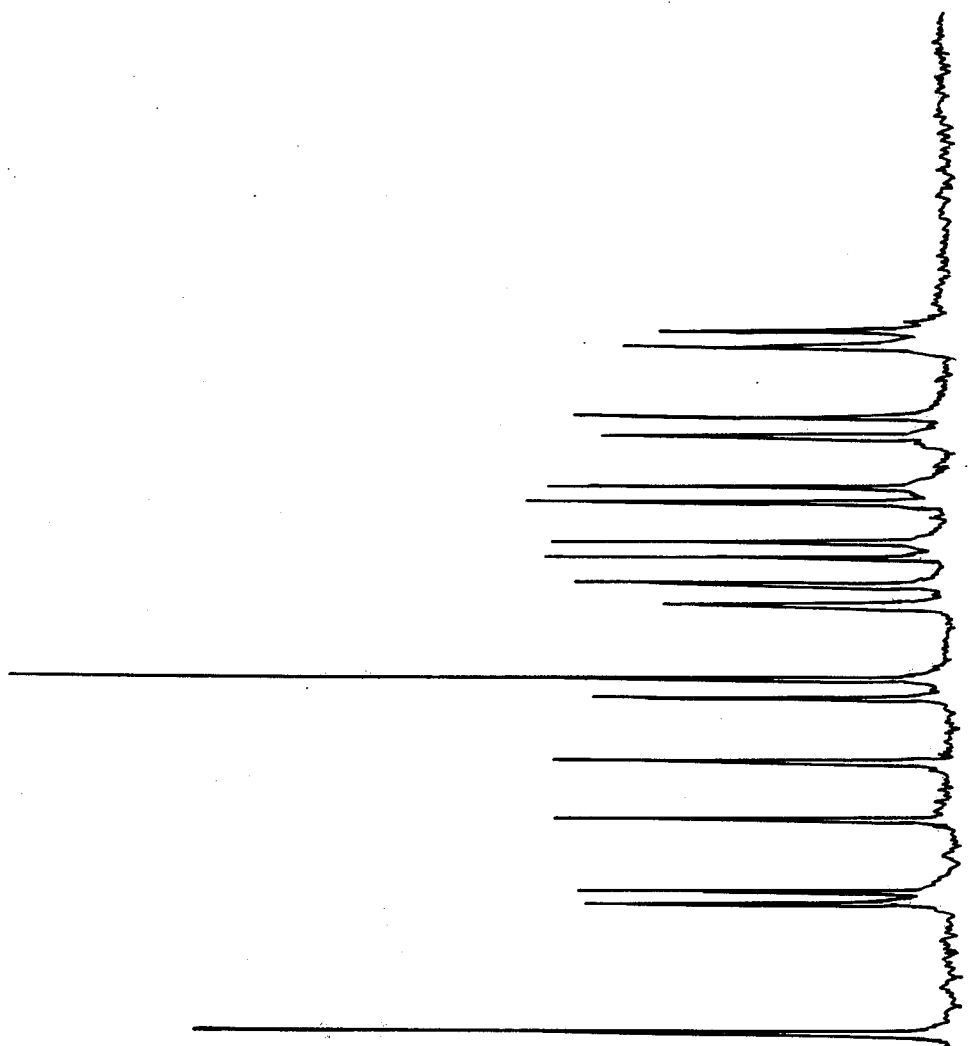
FIG. 2 shows $C^{13}$-CMR spectrum of 2'-deamino-3'-epiamino-3'-deoxy-XK-88-5 measured in deuterium oxide solution using dioxane as an internal standard.

7. PMR spectrum is shown in FIG. 1.
8. CMR spectrum is shown in FIG. 2.
9. Based on the foregoing physicochemical properties, the structural formula of 2'-deamino-3'-epiamino-3'-deoxy-XK-88-5 is considered to be as follows:

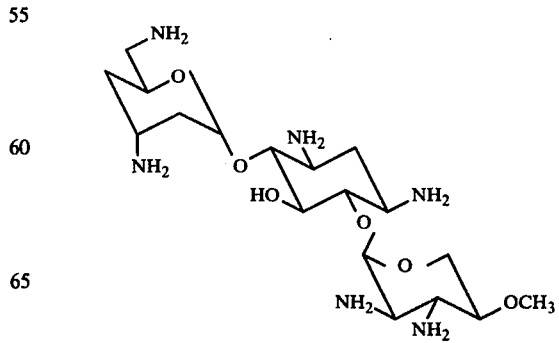

The resistant microorganisms referred to above, may be classified into the following groups. A resistant microorganism having an inactivating enzyme which is able to phosphorylate the hydroxyl group at the 3'-position of an aminoglycoside antibiotic, hereinafter such enzyme is referred to as APH(3')-I or II; a resistant microorganism having an inactivating enzyme which is able to acetylate the amino group at the 2'-position, hereinafter referred to as AAC(2'); a resistant microorganism having an inactivating enzyme which is able to acetylate the amino group at the 3-position, hereinafter referred to as AAC(3)-I; and a resistant microorganism having an inactivating enzyme which is able to nucleotydylate at the 2''-position, hereinafter referred to as ANT (2''), etc.

Code addresses of inactivating enzymes mentioned above are disclosed in Mitsuhashi: Drug Inactivating Enzymes and Antibiotic Resistance, Page 115 (Czechoslovak Medical Press, 1975).

In the field of the aminoglycoside antibiotics, it is known that some of the resistant microorganisms against aminoglycoside antibiotics are caused on R-factor and those microorganisms have inactivating emzymes.

Further, it is known that several chemical modification methods are effective to obtain effective derivatives which are more active potent than the original antibiotics against resistant microorganisms. Such resistant microorganisms, inactivating enzymes and chemical modification methods and various derivatives therefrom are disclosed in Kawaguchi et al.: Advances in Applied Microbiology, 18, 191-307 (1974). For example, disclosed in the same reference are derivatives such as, 3'-deoxy compounds, 3',4'-dideoxy compounds, 1-N-[α-hydroxy-γ-amino-butyryl]-compounds, etc. which are superior to the original antibiotic compound against the resistant microorganisms. However, there appears to be no recognition of a compound such as 2'-deamino-3'-epiamino-3'-deoxy-XK-88-5, which is an aminoglycoside antibiotic having an axial amino group at the 3'-position but not having substituent at the 2'- and 4'-positions.

Therefore, it is also an unexpected finding that the compound having a novel structural formula described above has superior antibacterial activities both against sensitive and resistant microorganisms.

Preparation of 2'-deamino-3'-epiamino-3'-deoxy-XK-88-5 from XK-88-5 is explained in detail below.

Process 1: preparation of 2'-deamino-3'-epiamino-3'-deoxy-XK-88-5 (Compound I) from a hexa-N-protected-2'-deamino-3'-epiamino-3'-deoxy-XK-88-5 (Compound II)

Compound I is obtained by eliminating the amino protecting groups of the Compound II. According to the kinds of amino protecting group containing in a starting compound (Compound II) a desired compound I is obtained by various elimination methods.

Three typical methods are as follows. The starting Compound II is obtained by Processes 2, 3 and 4 hereinafter mentioned.

(1) Where protecting groups of amino groups in Compound II is methoxycarbonyl, ethoxycarbonyl, acetyl or phthaloyl groups, etc., Compound I is obtained by hydrolyzing Compound II in water or a mixed solvent of water and alcohol with bases such as sodium hydroxide, potassium hydroxide, barium hydroxide, hydrazine, etc. at 50° to 170° C. for 0.5 to 24 hours, if necessary, in a sealed tube.

(2) Where protecting groups of amino groups in Compound II is benzyl or benzyloxycarbonyl groups, etc., Compound I is easily obtained by reacting Compound II with hydrogen gas of 1 to 5 by atmospheric pressure at 0° to 100° C. for 0.5 to 24 hours in the presence of catalysts such as palladium carbon, palladium black, Raney nickel, etc. in solvents such as methanol, ethanol, dioxane, etc.

(3) Where protecting groups of amino groups in Compound II is tertiarybutyloxycarbonyl or amyloxycarbonyl groups, etc., Compound I is obtained by reacting Compound II with acids such as trifluoroacetic acid, hydrochloric acid, etc.

Such elimination methods for protecting groups mentioned above are described in, for example, Capoor: Journal of Pharmaceutical Science, 59, pages 1-27 (1970).

Isolation and purification of the desired compound from the reaction mixture is carried out by conventional ion exchange, silica gel chromatography methods, etc.

Process 2: A preparation of a hexa-N-protected-XK-88-5 (Compound V) from XK-88-5

According to a known method, XK-88-5 is reacted with an amino protecting agent, to form Compound V at a temperature of −20° to 50° C., preferably 0° to 30° C., for 0.5 to 48 hours, preferably 1 to 24 hours in a solvent. As protecting agents acetic anhydride, methyl chloroformate, ethyl chloroformate, benzyloxycarbonyl chloride, benzaldehyde-sodium borohydride, tertiary butyloxycarbonyl azido, amyl chloroformate, N-ethoxycarbonylphthalimido, etc. may be used. Methoxycarbonyl, ethoxycarbonyl or benzyloxycarbonyl groups may be preferably used as an amino protecting group.

As solvents pyridine, dioxane, tetrahydrofuran, acetone, methanol, water, etc. may be used either alone or in combination.

A method for protecting amino groups by using the above-mentioned amino protecting agents is described, for example, in McOmie: Protective Groups in Organic Chemistry, pages 44-74 (Plenum Press, 1973) or Capoor: Journal of Pharmaceutical Science, 59, pages 1-27 (1970).

Isolation of the desired Compound V from the reaction mixture may be carried out by conventional methods for example, by concentration of solvents from the reaction solution, separation of the precipitated desired compound, washing of the desired compound and drying thereof. Process 3: A preparation of a hexa-N-protected-3'-0-sulfonyl-XK-88-5 (Compound VI) from the Compound V.

The Compound V obtained by process 2 is reacted with a sulfonyl chloride to form Compound VI at a temperature of 0° to 120° C., preferably 10° to 70° C., for 1 to 48 hours, preferably 3 to 24 hours in a solvent.

As sulfonyl chlorides, methanesulfonyl chloride, benzenesulfonyl chloride, paratoluenesulfonyl chloride, parabromobenzenesulfonyl chloride, etc. may be used.

The amount of the sulfonyl chloride utilized is from 0.5 to 15 mole-equivalents, preferably 1 to 10 mole-equivalents on the basis of the Compound V.

As solvents pyridine, collidine, lutidine, etc. may be used.

Isolation of Compound VI from the reaction mixture may be carried out as follows.

After completion of the reaction, water is added to the reaction mixture to decompose excess sulfonyl chloride, and then the solvent in the reaction mixture is removed. Then, a large amount of water is added to the residue and thus desired water-insoluble product is recovered by filtration. If necessary, after water and water-insoluble organic solvents such as chloroform, etc., are added to the residue, an organic solvent extraction may be carried out.

If necessary, further purification of the obtained Compound VI may be carried out by recrystallization or silica gel chromatography.

Process 4: A preparation of a hexa-N-protected-2'-deamino-3'-epiamino-3'-deoxy-XK-88-5 (Compound II) from the Compound VI Compound VI obtained by the process 3 is reacted with a metal hydride to form Compound II at a temperature of 0° to 150° C., preferably 20° to 100° C., for 1 to 48 hours, preferably 5 to 36 hours in a solvent.

As metal hydrides sodium borohydride, lithium borohydride, zinc borohydride, lithium triethylborohydride, sodium cyanoborohydride, tributyltin hydride, sulphurated sodium borohydride, lithium tributoxyaluminum hydride, lithium aluminum hydride, diborane, borane amine complex, aluminum hydride, lithium normal-butylcopper hydride, etc. may be used.

The amount of the metal hydride utilized is from 0.5 to 200 equivalents, preferably 1 to 100 equivalents on the base of the Compound VI.

As solvents benzene, toluene, N,N-dimethylformamide, dimethylsulfoxide, tetrahydrofuran, diethylether, methanol, pyridine, etc. may be used.

After completion of the reaction, if necessary, water is added to the reaction mixture to decompose excess metal hydride, and then the solvent in the reaction mixture is removed. Water and water-insoluble organic solvents such as chloroform, etc. are added to the residue and an organic solvent extraction may be carried out. A crude Compound II is obtained by removing the organic solvent used for extraction.

Further, in this process 4, compounds presumed as hexa-N-protected-3'-deoxy-XK-88-5, 1,3,6',2'',3''-penta-N-protected-2',3'-N-protected-epimino-2'-deamino-3'-deoxy-XK-88-5 and 1,3,6',2'',3''-penta-N-protected-2',3'-epimino-2'-deamino-3'-deoxy-XK-88-5 in addition to the Compound II, are prepared and extracted in the organic solvent at the same time.

Isolation and purification of the above-mentioned four compounds can be easily carried out by using a silica gel chromatography.

A reaction between a sulfonate of sugar and a metal hydride is described, for example, in Ball: Advances in Carbohydrate Chemistry and Biochemistry, 23, 269 (1968).

Minimum inhibitory concentrations (MIC) (mcg/ml) of the present compound were measured at pH 7.2 according to Standard Procedure of Japan Society of Chemotherapy and the results are shown in Table 1 in comparison with the starting material, XK-88-5.

Table 1

| Name of microorganism | Inactivating enzyme | Compound [I] present compound | (mcg/ml) XK-88-5 |
|---|---|---|---|
| Staphylococcus aureus Neuman | | 1.56 | 1.56 |
| Pseudomonas aeruginosa BmH#1 | | 6.25 | 6.25 |
| Pseudomonas aeruginosa BmH#10 | | 1.56 | 3.12 |
| Pseudomonas aeruginosa E-2 | | 25 | 25 |
| Providencia KY 3947 | | 12.5 | 12.5 |
| Providencia KY 3950 | | 50 | 100 |
| Escherichia coli $R_5$ | APH(3')-I,II | 6.25 | >100 |
| Escherichia coli $R_{16}$ | unknown | 1.56 | 100 |
| Escherichia coli $R_{18}$ | APH (3')-II | 12.5 | 25 |
| Escherichia coli $R_{19}$ | AAC(3)-I | 6.25 | 50 |
| Escherichia coli $R_{20}$ | APH(3')-I | 12.5 | >100 |
| Pseudomonas aeruginosa $R_4$ | AAC(3)-I | 25 | 100 |
| Pseudomonas aeruginosa $R_5$ | APH(3')-I,II | 12.5 | 25 |
| Pseudomonas aeruginosa $R_{10}$ | APH(3')-I | 12.5 | >100 |
| Pseudomonas aeruginosa $R_{11}$ | APH(3')-I,II | 50 | >100 |
| Providencia 164 | AAC(2') | 25 | >100 |
| Klebsiella pneumoniae Y-58 | ANT(2'') | 6.25 | 25 |

Note: Abbreviation in the column of Inactivating enzyme has the same meaning as defined above.

As is apparent from Table 1, the compound of the present invention is a useful substance which is expected to have an effect against infections caused by Gram-positive and Gram-negative microorganisms, particularly, the resistant microorganisms mentioned above.

The compound of the present invention is also useful as an antibacterial agent to clean and disinfect laboratory glassware and surgical instruments, and may also be used for pharmaceutical and sanitation purposes in cleaning and sanitizing hospital rooms and areas.

Non-toxic acid addition salts of the present compound also have as broad an antibacterial spectrum as the free base of the present compound, and similar effects can be expected.

Herein the non-toxic acid addition salts mean mono-, di-, tri-, tetra-, penta- and hexa-salts, which are formed by reaction of one molecule of 2'-deamino-3'-epiamino-3'-deoxy-XK-88-5 with 1 to 6 molecules of pharmaceutically acceptable non-toxic acid. Those pharmaceutically acceptable non-toxic acids include inorganic acids such as sulfuric acid, hydrochloric acid, hydrobromic acid, hydroiodic acid, phosphoric acid, carbonic acid, nitric acid, etc., and organic acids such as acetic acid, fumaric acid, maleic acid, malic acid, citric acid, succinic acid, mandelic acid, ascorbic acid, tartaric acid, etc. and amino acids such as aspartic acids, etc.

Practice of the certain specific embodiments of the present invention is illustrated by the following representative examples.

EXAMPLE 1

Preparation of hexa-N-ethoxycarbonyl-XK-88-5 (first step)

Into a mixed solvent consisting of 195 ml of water containing 45.6 g of anhydrous sodium carbonate and 195 ml of acetone was dissolved 13.50 g of XK-88-5 free base, and 43.2 g of ethyl chloroformate was slowly added thereto under water cooling (about 5° C.) with vigorous stirring. The reaction mixture was stirred vigorously for 30 minutes under water cooling (about 5° C.) and then stirred at 19° C. for 20 hours. White precipitate formed in the reaction mixture was filtered, and then sufficiently washed with 800 ml of water and 500 ml of ether, and dried in vacuo in the presence of phosphorus pentoxide, whereby 18.87 g of white powder of hexa-N-ethoxycarbonyl-XK-88-5 was obtained. Melting point: above 300° C. $[\alpha]_D^{17} = +76.1°$ (c=0.315; DMF).

Elemental analysis as $C_{36}H_{62}N_6O_{19}$: Found C, 48.50%, H, 7.20%, N, 9.36%. Calculated: C, 48.96%, H, 7.09%, N, 9.52%.

Preparation of hexa-N-ethoxycarbonyl-3'-0-(paratoluenesulfonyl)-XK-88-5 (second step)

Into 150 ml of pyridine was dissolved 3.00 g of hexa-N-ethoxycarbonyl-XK-88-5, obtained in the first step, and 9.90 g of paratoluenesulfonyl chloride was added thereto. After the resulting mixture was allowed to stand at 55° C.-65° C. for 23 hours, 10 ml of water was added thereto, and then pyridine and water were evaporated in vacuo. 150 ml of water was added to the resulting residue, and the mixture was stirred at room temperature for 30 minutes. Then, water-insoluble products were recovered by filtration, washed with 200 ml of water and 150 ml of ether, and dried in vacuo for about 16 hours, whereby 3.42 g of white powder of hexa-N-ethoxycarbonyl-3'-0-(paratoluenesulfonyl)-XK-88-5 was obtained. The analytical sample was recrystallized from water-ethanol.

Melting point: 193° C.-197° C.
$[\alpha]_D^{19} = +72.3°$ (c=0.361, DMF).
Elemental analysis as $C_{43}H_{68}N_6O_{21}S$: Found: C 49.51%, H 6.65%, N 8.08%, S 2.98% Calculated: C 49.79%, H 6.62%, N 8.10%, S 3.09%
IR spectrum (KBr disk method) 1175 cm$^{-1}$
PMR spectrum (solvent $d_6$-dimethylsulfoxide) $\tau$ 2.50 (quadraple lines, 4H), $\tau$ 7.60 (single line, 3H)

Preparation of hexa-N-ethoxycarbonyl-2'-deamino-3'-epiamino-3'-deoxy-XK-88-5 (third step)

Into 500 ml of dimethylsulfoxide was dissolved 25.0 g of hexa-N-ethoxycarbonyl-3'-0-(paratoluenesulfonyl)-XK-88-5, obtained by the same process as in the second step above, and 12.5 g of sodium borohydride was added thereto. The resulting mixture was heated in an oil-bath (65° C.) for 17 hours. Dimethylsulfoxide was removed under reduced pressure and 600 ml of water was added to the resulting residue and then the extraction was carried out with ten 300 ml portions of chloroform. The resulting chloroform layers were combined and washed with three 50 ml portions of water. The resulting chloroform layer was dried over anhydrous sodium sulfate and chloroform was removed under reduced pressure. The resulting residue was purified by passing through a column packed with 2.20 kg of silica gel. The eluate was taken in 200 ml portions. Elution was carried out with chloroform-methanol (30 : 1 by volume), chloroformmethanol (20 : 1 by volume) and chloroform-methanol (10 : 1 by volume) for fraction Nos. 1-101, Nos. 102-199 and Nos. 200-269, respectively. After evaporating the solvent, 4.20 g of hexa-N-ethoxycarbonyl-3'-deoxy-XK-88-5 was obtained from fraction Nos. 56-72.

Further, 3.40 g of hexa-N-ethoxycarbonyl-2'-deamino-3'-epiamino-3'-deoxy-XK-88-5 was obtained from fraction Nos. 77-108.

Melting point: 237-241° C. $[\alpha]_D^{22} = +63.0°$ (C=0.437, DMF)

Elemental analysis as $C_{36}H_{62}N_6O_{18}$: Found: C, 49.87%, H, 7.22%, N, 9.70%, S, 0.00%. Calculated: C, 49.97%, H, 7.44%, N, 9.61%, S, 0.00%.

Furthermore, 4.55 g of 1,3,6',2'',3''-penta-N-ethoxycarbonyl-2',3'-ethoxycarbonyl epimino-2'-deamino-3'-deoxy-XK-88-5 was obtained from fraction Nos. 109-138 which were eluted subsequently to the above fractions. Additionally, 3.10 g of 1,3,6',2'',3''-penta-N-ethoxycarbonyl-2',3'-epimino-2'-deamino-3'-deoxy-XK-88-5 was obtained from fraction Nos. 196-231.

The product having N-ethoxycarbonyl aziridine ring at the 2',3'-position was presumed as an intermediate, that is, it is presumed that Compound (V) or hexa-N-ethoxycarbonyl-3'-deoxy-XK-88-5 was produced through the intermediate from Compound [IV] in the present reaction step.

Preparation of 2'-deamino-3'-epiamino-3'-deoxy-XK-88-5 (fourth step)

Into 170 ml of potassium hydroxide adjusted to 5.1 N with water-methanol (1 : 1 by volume) was dissolved 2.50 g of hexa-N-ethoxycarbonyl-2'-deamino-3'-epiamino-3'-deoxy-XK-88-5 obtained in the third step, and was heated in a sealed tube at the temperature of 140° C. for 14 hours. After the completion of the reaction, the reaction mixture was adjusted to pH 4 with concentrated hydrochloric acid under ice cooling, and the resulting precipitate was removed by filtration and washed with 70 ml of methanol-water (1 : 1 by volume). The thus obtained filtration and washings were combined and were concentrated under reduced pressure to about 20 ml. The resulting concentrate was readjusted to pH 4.0 and then was purified by passing through a column packed with 350 ml of Amberlite CG-50 (ammonium form) (Product of Rohm and Haas Co., U.S.A.). After washing with 1000 ml of water, the eluate was taken in 22 ml portions. Elution was carried out with 0.1 N aqueous ammonia, 0.2 N aqueous ammonia and 0.3 N aqueous ammonia for fraction Nos. 1-63, Nos. 64-124 and Nos. 124-183, respectively. After evaporating the solvent, 0.70 g of 2'-deamino-3'-epiamino-3'-deoxy-XK-88-5 was obtained from fraction Nos. 101-166. Melting point: 134-137° C.
$[\alpha]_D^{22} = +106°$ (c=0.356, water).

Elemental analysis as $C_{18}H_{38}N_6O_6.H_2CO_3.H_2O$: Found: C, 44.75%, H, 8.08%, N, 16.55%. Calculated: C, 44.34%, H, 8.24%, N, 16.33%.

On silica gel thin layer chromatography, Rf value was 0.83 (developer:methanol:conc. aqueous ammonia: chloroform = 3:2:1 by volume), presuming the Rf value of XK-88-5 as 1.00. Molecular weight determined by high resolution-mass spectometry: 434.2816.

Mass spectrum: m/e: 129, 145, 163, 273, 307

PMR spectrum and CMR spectrum are shown in FIGS. 1 and 2, respectively.

EXAMPLE 2

Preparation of 2'-deamino-3'-epiamino-3'-deoxy-XK-88-5 sulfate

Into 10 ml of water was dissolved 1.00 g of 2'-deamino-3'-epiamino-3'-deoxy-XK-88-5 obtained according to the method as in Example 1 and the solution was adjusted to pH 3.0 with sulfuric acid. 100 ml of acetone was added thereto with stirring and the resulting white precipitate was recovered by filtration, washed with 20 ml of acetone-water (10 : 1 by volume) and dried in vacuo, whereby 1.31 g of 2'-deamino-3'- epiamino-3'-deoxy-XK-88-5 trisulfate was obtained. Melting point: 197-205° C.

$[\alpha]_D^{22} = +58.2°$ (c=0.300, water).

Reference 1

Reduction of hexa-N-ethoxycarbonyl-3'-0-(paratoluenesulfonyl)-XK-88-5 with lithium aluminium hydride.

Into 0.5 ml of dimethylsulfoxide was dissolved 23 mg of hexa-N-ethoxycarbonyl-3'-0-(paratoluenesulfonyl) XK-88-5 and 12 mg of lithium aluminum hydride was added thereto and the solution was heated in an oil-bath (65-68° C.) for 14 hours. The resulting reaction mixture was subjected to a thin layer chromatography. The reaction mixture was developed on a silica gel thin layer plate made by Merck [developer:chloroform-methanol (18:1 by volume)], as the result of the thin layer chromatography above described the spots corresponding to hexa-N-ethoxycarbonyl-3'-deoxy-XK-88-5 (Rf: 0.59), 1,3,6',2'',3''-penta-N-ethyoxycarbonyl-2',3',-N-ethoxycarbonylepimino-2'-deamino-3'-deoxy-XK-88-5 (Rf: 0.52) and 1,3',6',2'',3'''-penta-N-ethoxycarbonyl 2',3'-epimino-2'-deamino-3'-deoxy-XK-88-5 were detected.

What is claimed is:

1. 2'-deamino-3'-epiamino-3'-deoxy-XK-88-5 represented by the formula:

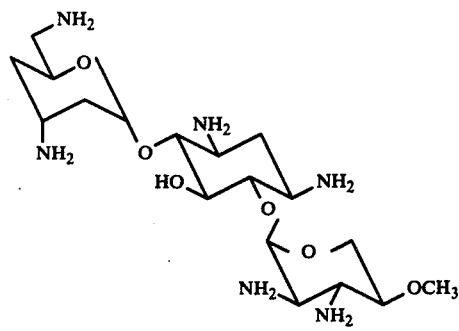

and pharmaceutically acceptable acid addition salts thereof.

2. A pharmaceutically acceptable acid addition salt of the compound of claim 1 selected from the group consisting of the sulfate, hydrochloride, hydrobromide, hydroiodide, phosphate, carbonate, nitrate, acetate, fumarate, maleate, malate, citrate, succinate, mandelate, ascorbate, tartarate and aspartate.

* * * * *